United States Patent
Fuda et al.

(10) Patent No.: US 6,743,957 B2
(45) Date of Patent: Jun. 1, 2004

(54) METHOD OF TREATING FLUORINE COMPOUND

(75) Inventors: Kiyoshi Fuda, Akita (JP); Toshiaki Matsunaga, Akita (JP); Takeshi Na Kamiya, Akita (JP); Kota Omori, Akita (JP)

(73) Assignee: JEMCO, Inc., Akita (JP)

( * ) Notice: Subject to any disclaimer, the term of this patent is extended or adjusted under 35 U.S.C. 154(b) by 142 days.

(21) Appl. No.: 10/070,756

(22) PCT Filed: Jul. 26, 2001

(86) PCT No.: PCT/JP01/06451

§ 371 (c)(1),
(2), (4) Date: Jun. 26, 2002

(87) PCT Pub. No.: WO02/10104

PCT Pub. Date: Feb. 7, 2002

(65) Prior Publication Data

US 2003/0006195 A1 Jan. 9, 2003

(30) Foreign Application Priority Data

Jul. 27, 2000 (JP) .......................................... 2000-227191
Jul. 6, 2001 (JP) .......................................... 2001-206241

(51) Int. Cl.$^7$ .............................................. C07C 17/38
(52) U.S. Cl. ....................... 570/179; 570/140; 570/142; 570/153; 570/175; 570/177
(58) Field of Search ................................. 570/140, 142, 570/153, 175, 177, 179

(56) References Cited

U.S. PATENT DOCUMENTS 4,282,162 A     8/1981     Kuhls

FOREIGN PATENT DOCUMENTS

| JP | 6-48742 | 2/1994 |
|---|---|---|
| JP | 10-279307 | 10/1998 |
| WO | 94/10973 | 5/1994 |

*Primary Examiner*—Johann R. Richter
(74) *Attorney, Agent, or Firm*—Oblon, Spivak, McClelland, Maier & Neustadt, P.C.

(57) ABSTRACT

Divalent and trivalent metal salts are added to the solution containing the fluorine compound and the polymer containing fluorine to precipitate the layered double hydroxide containing the fluorine compound between layers. At this time, the polymer containing fluorine suspended in the solution is also coagulated to precipitate. By these processes, the fluorine compound is fixed with high rate to separate from the solution with the polymer containing fluorine, and recovered if necessary. By this treatment process, the fluorine compound and the polymer containing fluorine, contained in the wastewater etc. can be separated easily, and the burden to environment or ecosystem can be reduced.

20 Claims, No Drawings

METHOD OF TREATING FLUORINE COMPOUND

FIELD OF THE INVENTION

Present invention relates to a treatment process reducing a burden to environment and ecosystem about a solution containing a molecular anion having a per-fluorocarbon chain as a main component and a polymer containing fluorine. In addition, it is preferable that said treatment process recovers the above-mentioned anion to use effectively. Specifically, the present invention relates to a technology, which forms a layered double hydroxide to fix the molecular anion having the per-fluorocarbon chain as a main component and the polymer containing fluorine in the solution, and recovers to reproduce these anions preferably.

BACKGROUND OF THE INVENTION

An anion surface-active agent having the per-fluorocarbon chain as a main component is used as an indispensable material of a production process in many fields, such as an emulsion polymerization process of PTFE (poly-tetra-fluoro-ethylene) and a production process of an electronic parts industry. Moreover, said anion surface-active agent is also widely used as a material, which are various paints, a coating agent, and a fire-extinguishing agent, etc. However, in these production processes, the above-mentioned anion surface-active agent has been used as a dilute solution, such as several % to 0.01% by weight. Especially, for example, in the emulsion polymerization of PTFE, a lot of fine particles of PTFE resins to the fluorine anion surface-active agent have suspended in a solution, so that the efficient fixing and recovering on an industrial scale has been difficult. Moreover, the problem of this fixing and recovering has not been considered in general because this solution is dilute. Furthermore, the fluorine compound, such as said anion surface-active agent, is a hard material to be processed by the activated sludge processing, which has been widely used as a wastewater processing. However, a harmony of chemical materials to environment or ecosystem is required strongly in recent years, and, also about this fluorine compound, it is started that the necessity of the technology about the closing system by fixing, recovering and reproducing is recognized strongly.

According to the fixing and recovering of this anion surface-active agent, the technology using the layered double hydroxide has been examined to be in practical use about a phosphate anion or an organic anion, as a scavenger or a removal agent of anions. However, about molecular anion having the per-fluorocarbon chain as a main component, such examinations have not been done previously. In addition, as a conventional technology, it is known that the process, in which an ammonium salt of fluoroalkane acid is extracted to recover by using an organic solvent, such as dichloro-methane or trichloro-methane, was proposed (Japanese Patent Raid Open No. Shou 61-215346), but this process uses an organic solvent containing chlorine, so that it is not enough for reducing the burden to environment. Moreover, by this process, it is necessary to remove the fine particles of PTFE, which are suspended in the solution, so that the processing takes time and effort Furthermore, although it is also known that the other process was proposed, in which fluoroalkane acid was recovered by an ion exchange (WO99/62858, UK1314607), it is also necessary to remove the fine particles of PTFE beforehand in this process.

In addition, the inventors have already reported the layered double hydroxide having anion between layers ($Zn_2Al(OH)_6C_7F_{15}CO_2$) for the purpose of a material synthesis (the 76th spring annual meeting of the Chemical Society of Japan), about a high concentration aqueous solution of per-fluoro-octanoic acid ammonium (about 8.6% by weight). However, this report was not for the purpose of fixing and recovering of the anion like this invention, about the solution having the wide concentration range including the dilute solution of 0.1% by weight. Therefore, the process about absorbing or fixing of such fluorine compound has not been reported yet.

[Disclosure of the Invention]

Present invention provides the treatment technology, about the solution containing the fluorine compound having the per-fluorocarbon chain and the polymer containing fluorine, in which the layered double hydroxide having the fluorine compound is formed to precipitate with the polymer containing fluorine simultaneously. In addition, it is preferable that said treatment technology fixing to recover efficiently the anion having the per-fluorocarbon chain as the main component, such as carboxylic acid ion, sulfonic acid ion, etc., from the aqueous solution having the wide concentration range including the dilute aqueous solution of 0.1% by weight.

That is, this invention provides the process comprising the following constitutions.

[1] A treatment process of a solution containing an organic compound having a fluorocarbon chain (hereinafter said to as the fluorine compound) and a polymer containing fluorine, the process comprising,
adding divalent and trivalent metal salts to said solution,
forming a layered double hydroxide having the fluorine compound between layers to fix the fluorine compound, and
precipitating said layered double hydroxide with the polymer containing fluorine.

[2] A treatment process of a solution containing the fluorine compound and a polymer containing fluorine, the process comprising,
adding divalent and trivalent metal salts to said solution,
forming a layered double hydroxide having the fluorine compound between layers to fix the fluorine compound,
precipitating said layered double hydroxide having the fluorine compound between layers and the polymer containing fluorine,
recovering a solid part by a solid-liquid separation,
dissolving said recovered solid part in an acid, and
separating a fluorine compound or its salt.

[3] The treatment process of the solution containing the fluorine compound and the polymer containing fluorine according to above mentioned process [1] or [2], the process further comprising,
adjusting pH of the solution to more than 4,
precipitating the layered double hydroxide having the fluorine compound between layers and the polymer containing fluorine compound.

[4] The treatment process of the solution containing the fluorine compound and the polymer containing fluorine according to above-mentioned process [1] or [2], the process further comprising,
adding an alkali to the solution to adjust pH from 4 to 12,
adding divalent and trivalent metal salts to said solution, and precipitating the layered double hydroxide having the fluorine compound between layers and the polymer containing fluorine.

[5] The treatment process of the solution containing the fluorine compound and the polymer containing fluorine according to any one of above-mentioned processes [1] to [4], wherein the divalent metal salt is a salt of magnesium, calcium, zinc, nickel, copper, manganese (divalent), or cobalt (divalent), and the trivalent metal salt is a salt of aluminum, iron, chromium, manganese (trivalent), cobalt (trivalent), potassium, lanthanum, or scandium.

[6] The treatment process of the solution containing the fluorine compound and the polymer containing fluorine according to any one of above-mentioned processes [1] to [5], wherein the divalent and the trivalent metal salts are chlorides.

[7] The treatment process of the solution containing the fluorine compound and the polymer containing fluorine according to any one of above-mentioned processes [1] to [6], wherein said fluorine compound is carboxylic acid or sulfonic acid having the fluorocarbon chain, in which the number of carbon is more than 5.

[8] The treatment process of the solution containing the fluorine compound and the polymer containing fluorine according to any one of above-mentioned processes [1] to [7], wherein the polymer containing fluorine is poly-tetra-fluoro-ethylene.

[9] The treatment process of the solution containing the fluorine compound and the polymer containing fluorine according to any one of above-mentioned processes [1] to [8], wherein the layered double hydroxide having the fluorine compound between layers is shown in the following formula [1].

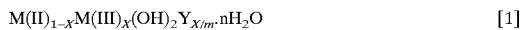

$$M(II)_{1-x}M(III)_x(OH)_2Y_{x/m} \cdot nH_2O \qquad [1]$$

where Y is an anion having valence number m of the fluorine compound having the fluorocarbon chain, M(II) is a divalent metal ion, M(III) is a trivalent metal ion, X is 0.1 to 0.5, and n is 0 or positive integer.

[10] A treatment process for recovering the fluorine compound and its salts, the process comprising,
precipitating the layered double hydroxide and the polymer containing fluorine by the treatment process according to any one of above mentioned processes [1] to [9],
recovering the solid part by the solid-liquid separation,
dissolving said recovered solid part in a mineral acid to recover the separated fluorine compound or its salts, or
heating said mineral acid dissolving the recovered solid part,
putting quietly to separate an oil layer, and
taking out an oil layer to recover the fluorine compound and its salts.

[11] A treatment process for recovering the fluorine compound and its salts, the process comprising,
precipitating the layered double hydroxide and the polymer containing fluorine by the treatment process according to any one of above mentioned processes [1] to [9],
recovering the solid part by the solid-liquid separation,
contacting said separated solid part with a sodium carbonate aqueous solution,
recovering the solid part by the solid-liquid separation,
dispersing the recovered solid part to an organic solvent, and
filtering an insoluble solid part from said solvent.

According to the above-mentioned processes of the present invention, the fluorine compound can be fixed stably, to form the precipitate of the layered double hydroxide (LDH) having the fluorine compound between layers, by adding divalent and trivalent metal salts to the solution containing the fluorine compound, such as the surface-active agent having the per-fluorocarbon chain, and the polymer containing fluorine. Moreover, since the polymer containing fluorine is precipitated with said LDH simultaneously, the polymer containing fluorine can be removed from the solution with LDH by the solid-liquid separation.

In addition, according to the treatment process of the present invention, even when the concentration of the anion aqueous solution of the surface-active agent having the per-fluorocarbon chain is less than several % by weight, for example, very low concentration of about 0.01% by weight, this fluorine compound can be fixed with a very high rate of more than 90%. Moreover, as the adding metal salt, the safe salt to environment can be used, and the recovered layered double hydroxide is a solid, so that it can be processed advantageously in transportation or storage by drying.

Hereafter, this invention is explained concretely.

(A) Formation of the Layered Double Hydroxide

Present invention is the treatment process, wherein the divalent and trivalent metal salts are added to the aqueous solution containing the anion of the organic fluorine compound having the fluorocarbon chain (the fluorine compound), such as carboxylic acid ion or sulfonic acid ion, etc., and the polymer containing fluorine, such as PTFE, to form LDH containing said anion between the layers. By this process, the above-mentioned anion is fixed between the layers of LDH, and the polymer containing fluorine is precipitated simultaneously. In addition, said precipitate is recovered by the solid-liquid separation from the solution. Specifically, for example, the treatment process of the present invention can be applied effectively to the solution, in which a fluorine surface-active agent, such as carboxylic acid, is contained as the fluorine compound having the fluorocarbon chain, and poly-tetra-fluoro-ethylene is contained as the polymer containing fluorine. Moreover, as said solution containing the fluorine compound and the polymer containing fluorine, a coagulated wastewater after an emulsion polymerization of poly-tetra-fluoro-ethylene resin can be mentioned.

In the present invention, for example, the layered double hydroxide having the fluorine compound between the layers is the compound shown in the following formula [1]. In addition, it is available that this compound contains water or not.

$$M(II)_{1-x}M(III)_x(OH)_2Y_{x/m} \cdot nH_2O \qquad [1]$$

where Y is the anion having the valence number m of the fluorine compound having the fluorocarbon chain, M(II) is the divalent metal ion, M(III) is the trivalent metal ion, X is 0.1 to 0.4, and n is 0 or positive integer.

The layered double hydroxide of above formula [1] having the fluorine compounds between layers is, for example, the compound that the anion A is replaced by the fluorine compound Y having the fluorocarbon chain, in the compound of the following formula [2].

$$M(II)_{1-x}M(III)_x(OH)_2A_{x/m} \cdot nH_2O \qquad [2]$$

where A is the anion having the valence number m, M(II), M(III), X, and n are the same as the formula [1].

The divalent metal ion is each ion of magnesium, calcium, zinc, nickel, copper, manganese (divalent), or cobalt (divalent). Moreover, the trivalent metal ion is each ion of aluminum, iron, chromium, manganese (trivalent), cobalt (trivalent), gallium, lanthanum, or scandium. A chloride, a sulfate, or a nitrate, etc., can be used as the sources of these ions. In these compounds, since the chloride is easy to receive and its reaction effect is also good, it is preferably to be used. Moreover, it is also available that these metal salts are the mixed compounds having two or more kinds of ion respectively. As the anion having the valence number m, carboxylic acid ion, sulfonic acid ion, chlorine ion and nitric acid ion etc. can be used.

The layered double hydroxide shown in the above-mentioned formula [1] can be formed by adjusting pH to more than 4, preferably 5 to 8, and adding above-mentioned divalent and trivalent metal salts to the aqueous solution of the fluorine compound having the fluorocarbon chain. In addition, it is preferable that the addition of the metal salts is after or the same time at the adjustment of pH. Specifically, for example, the above-mentioned layered double hydroxide is precipitated by the way that the aqueous solution mixed with the above-mentioned divalent and trivalent metal salts is dropped gradually in the aqueous solution of the fluorine compound having the fluorocarbon chain, until the mole ratio becomes to the formula [1], and simultaneously alkali is dropped gradually to adjust pH of the solution to more than 4, preferably 5 to 8. Moreover, as alkali, conventional sodium hydroxide, and potassium hydroxide etc. can be used. In addition, when the divalent metal ion is calcium or magnesium, it is available that pH of the aqueous solution is in the range of 5 to 12. Regarding the addition of the divalent and trivalent metal salts, it is preferable that X value of mole ratio is 0.1 to 0.5 in the above-mentioned formula [1]. Usually, it takes about 3 hours for a natural precipitation of the separated substance at room temperature. In addition, it is preferable that the solution is stirred. The formed precipitate can be filtered to recover.

In the above-mentioned layered double hydroxide, the layered double hydroxide having the X value of about 0.33 in the formula [1], is not only having the large amount of the reception capacity (the absorption capacity), but also making the stable compound between the absorbed anion and itself Therefore, said layered double hydroxide is the most preferable for fixing and recovering the absorbed anion. Moreover, both of the divalent metal ion of zinc or magnesium and the trivalent metal ion of aluminum or iron, which can form the layered double hydroxide, are safe and harmless to environment. In addition, chlorine ion and Na ion used in the forming process of this layered double hydroxide are also safe and harmless to environment. Furthermore, by controlling pH of the aqueous solution to near neutral, the influence to environment by the wastewater can also be removed substantially.

In addition, as mentioned above, when the precipitate of the layered double hydroxide having fluorine compound between layers is formed, before or while adjusting pH of the solution and adding the metal salts, it is preferable that the inert gas is bubbled beforehand in the solution containing the fluorine compound and the polymer containing fluorine to drive out the carbonic acid contained in the solution. If the carbonic acid is remained in the solution, the metal salts and the alkali will react with carbonic acid, so that it is not preferable.

According to the above-mentioned process for forming the layered double hydroxide, the objective anion of the fluorine compound having the fluorocarbon chain can be fixed with high efficiency of more than 60%, preferably more than 90%. Moreover, according to the treatment process of the present invention, the polymer containing fluorine in the solution is coagulated to precipitate, with the layered double hydroxide. From this process, it is supposed that the above-mentioned layered double hydroxide is reacted as a coagulant.

In addition, the formed precipitate containing the layered double hydroxide can be separated by the conventional method of the solid-liquid separation. As the concrete separation equipment or method, for example, the filtering, a decantation, a centrifugation, a thickener, a filter press, a precoat, and a body field, etc. can be used. In addition, it is not limited to these.

(B) Recovering the Fluorine Compound

The process for separating the fluorine compound from the recovered layered double hydroxide shown with the formula [1] is the followings. The precipitate of this layered double hydroxide is dissolved in the mineral acid having pH of less than 1. At this time, since the fluorine compound is remained in the strong acid without dissolving, this remained fluorine compound is recovered by the solid-liquid separation. On the other hand, when the liquid temperature of this solution is more than the fusion temperature of the fluorine compound or its salt, since this fluorine compound is liquefied, the fluorine compound or its salt can be recovered by putting quietly to take out the separated oil layer. Moreover, since the polymer containing fluorine, which is coagulated to precipitate together with the layered double hydroxide, is remained in the strong acid without dissolving, the polymer containing fluorine can be separated as the solid part, by setting the liquid temperature to more than the fusion temperature of the fluorine compound or its salt to liquefy the fluorine compound.

Specifically, for example, the coagulated precipitate of the precipitated layered double hydroxide and the polymer containing fluorine, are recovered by the solid-liquid separation, and the recovered substance was dissolved in sulfuric acid etc. having pH of less than 1. At this time, the divalent and trivalent metal components in the layered double hydroxide are dissolved. Moreover, when the liquid temperature is higher than the fusion temperature of the fluorine compound or its salt, the fluorine compound or its salt is liquefied. On the other hand, since the coagulated substance of the polymer containing fluorine contained in the precipitate, is not dissolved in the strong acid, the coagulated polymer containing fluorine, which is the solid part, can be separated, by the solid-liquid separation of the solution, while keeping the liquid temperature of more than the fusion temperature. Therefore, as putting quietly this solution at more than the fusion temperature, the water layer containing the divalent and trivalent metal ions and the oil layer containing the fluorine compound or its salt can be separated to take out this oil layer. According to such separation of liquid and liquid, the polymer containing fluorine and the fluorine compound can be separated easily. The fluorine compound, such as carboxylic acid, can be recovered with high purity and high yield by refining this oil layer by the distillation, etc.

In addition, when the precipitated layered double hydroxide and the coagulated precipitate of the polymer containing fluorine, are mixed with sulfuric acid etc. having pH of less than 1, the temperature of the solution is raised by heating of dilution generally. From-this reason, when the liquid temperature becomes more than the fusion temperature of the fluorine compound or its salt, it is preferable that the filtrate containing the liquefied fluorine compound and the coagulated polymer containing fluorine, which is the solid part, can be separated by the solid-liquid separation to keep the temperature. Moreover, when the liquid temperature is low, it is preferable that said liquid is heated, so that it may become more than the fusion temperature.

As another process, it is also available that the fluorine compound and the polymer containing fluorine are separated as the solid part, by the solid-liquid separation of the solution, where the precipitate was dissolved in the strong acid, at the liquid temperature of less than the fusion temperature. Then, the recovered solid part is heated more than the fusion temperature to liquefy the fluorine compound, so that the coagulated polymer containing fluorine, which remains as the solid part, is separated from the solution.

The recovery process using the ion exchange can be used, other than the above-mentioned process, where the precipitate is dissolved in the strong acid. That is, the precipitate containing the layered double hydroxide etc., which is separated by the solid-liquid separation, is dispersed in the aqueous solution of carbonate, such as sodium carbonate. At this time, the divalent and trivalent metal ions, which have been fixed in the layered double hydroxide, are ion-exchanged by the carbonate ion, and to be eluted in the liquid. Then, the solid part is recovered by the solid-liquid separation of said solution and dissolved in an alcohol. The insoluble solid part in the alcohol is filtered, so that the fluorine compound or its salt can be recovered.

When the recovered solid part is contacted with the alcohol, although the fluorine compound, such as carboxylic acid, is dissolved in the alcohol, the coagulated polymer containing fluorine is not dissolved to remain as the solid part. This alcoholic solution of the fluorine compound is refined by the distillation, etc., so that the fluorine compound, such as carboxylic acid, can be recovered with high purity and high yield. On the other hand, the coagulated precipitate of the polymer containing fluorine can be recovered by the conventional method of the solid-liquid separation. As this separation equipment or method, the filtering, the decantation, the centrifugation, the thickener, the filter press, the precoat, the body field, etc. can be used. In addition, it is not limited to these.

(C) Applications

As mentioned above, according to the treatment process of the present invention, the fluorine compound can be fixed by forming the layered double hydroxide having the fluorine compound between layers, and the polymer containing fluorine suspending in the solution can also be coagulated to precipitate with the formation of the precipitation of the fluorine compound. Moreover, when the wastewater contains the anions, which are easy to form LDH, such as the carbonate ion and the sulfate ion, as an inter layer substance, the process of the present invention can be applied effectively by putting more superfluous amount of the metal salts than the inter layer anions, into the solution.

Furthermore, according to the treatment process of the present invention, the process of the present invention can be developed into the various methods, such as the ion exchanging method, in which the fluorine compound is absorbed and fixed on the preformed layered double hydroxide having good ion exchange ability shown in the above-mentioned formula [2], and a re-hydrating method, in which the compound, where the fluorine compound is absorbed and fixed, is baked to reproduce the absorption ability for reusing, etc.

The treatment process of the present invention is explained concretely with the following examples. In addition, these examples are measured under the following conditions. The concentration of the negative ion in the aqueous solution was measured by the colorimetric method using LC/MS analysis or methylene-blue. The calibration curve was made by following ways. Five kinds of standard solution, in which 1 to 5 ppm by weight of ammonium salt of the above-mentioned negative ions was contained, were prepared, and 30 ml of said standard solution was taken respectively to the separatory funnels to be added 10 ml of chloroform and 10 ml of methylene-blue solution. After shaking well, these solutions were put quietly for 10 minutes and the calibration carve was made by measuring the each absorbance of these solutions using a visible/ultraviolet spectrometer. The measuring wavelength was fixed at 635 nm. The absorbance value was in the range of 0 to 1 in this concentration range, and the calibration curve showed good linearity. The conditions of the examples and the results are shown in table 1.

EXAMPLE 1

Al—Zn System

Regarding the coagulated wastewater of the poly-tetra-fluoro-ethylene resin after the emulsion polymerization, where the PTFE concentration was 2300 ppm, the concentration of per-fluoro-octanoic acid ammonium ($C_7F_{15}COONH_4$) was measured to be 148 ppm. The sodium hydroxide aqueous solution of 0.2N was added to this wastewater to adjust pH to 7. The liquid temperature was 26° C. Next, about 10 mL of the mixed aqueous solution of aluminum chloride and zinc chloride was dropped in 1 L of the wastewater for 3 hours, wherein $Al^{3+}$ ion was 0.378 mmol (1.1 times mol of APF0 in the wastewater), and $Zn^{2+}$ ion was 0.755 mmol (2.2 times mol of APF0 in the wastewater), in this mixed aqueous solution. In addition, this aqueous solution was stirred by 50 rpm using an anchor aerofoil while dropping. Moreover, while dropping, the sodium hydroxide aqueous solution of 0.2N was dropped suitably to adjust pH from more than 6.5 to less than 7.5. From immediately after dropping the mixed aqueous solution of aluminum chloride and zinc chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 μm. This precipitate was dried at 70° C. for 15 hours with the filter paper. The weight of the dried precipitate was 2.50 g. When the dried precipitate was analyzed by a differential thermogravimetric analysis (DTA), an infrared absorption spectrum (IR), and XRD, the peaks belonging to the poly-tetra-fluoro-ethylene resin, the negative ion surface-active agent, i.e., per-fluoro-octanoic acid, and the layered double hydroxide were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 2 ppm. Therefore, the fixing ratio of the per-fluoro-octanoic acid contained in the layered double hydroxide was 98.6%. Moreover, the concentration of poly-tetra-fluoro-ethylene in the supernatant liquor was less than 50 ppm, so that the precipitation rate was more than 98%.

EXAMPLE 2

Al—Mg System

Regarding the coagulated wastewater of the poly-tetra-fluoro-ethylene resin after the emulsion polymerization, wherein PTFE concentration was 2300 ppm, the concentration of per-fluoro-octanoic acid ammonium ($C_7F_{15}COONH_4$) was measured to be 200 ppm. The sodium hydroxide aqueous solution of 0.2N was added to this wastewater to adjust pH to 10. The liquid temperature was 26° C. Next, about 10 mL of the mixed aqueous solution of aluminum chloride and magnesium chloride was dropped in 1 L of this wastewater for 3 hours, wherein $Al^{3+}$ ion was 0.603 mmol (1.3 times mol of APFO in the wastewater) and $Mg^{2+}$ ion was 1.21 mmol (2.6 times mol of APFO in the wastewater) in the mixed aqueous solution. In addition, this aqueous solution was stirred by 100 rpm using the anchor aerofoil while dropping. Moreover, while dropping, the sodium hydroxide aqueous solution of 0.2N was dropped suitably to adjust pH from more than 9 to less than 10. From immediately after dropping the mixed aqueous solution of aluminum chloride and magnesium chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 µm. This precipitate was dried at 70° C. for 15 hours with the filter paper. The weight of the dried precipitate was 2.54 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 8 ppm. Therefore, the fixing ratio of the per-fluoro-octanoic acid contained in the layered double hydroxide was 95.9%. Moreover, the concentration of poly-tetra-fluoro-ethylene of the supernatant liquor was less than 50 ppm, and this precipitation rate was more than 98%.

EXAMPLE 3

Al—Mg System, Superfluous Addition

Regarding the coagulated wastewater of the poly-tetra-fluoro-ethylene resin after the emulsion polymerization, wherein PTFE concentration was 2300 ppm, the concentration of per-fluoro-octanoic acid ammonium ($C_7F_{15}COONH_4$) was measured to be 148 ppm. The sodium hydroxide aqueous solution of 0.2N was added to this wastewater to adjust pH to 7. The liquid temperature was 26° C. Next, about 10 mL of the mixed aqueous solution of aluminum chloride and magnesium chloride was dropped in 1 L of said wastewater for 3 hours, wherein $Al^{3+}$ ion was 4.46 mmol (13 times mol of APFO in the wastewater) and $Mg^{2+}$ ion was 8.92 mmol (26 times mol of APFO in the wastewater) in the mixed aqueous solution. In addition, this aqueous solution was stirred by 100 rpm using the anchor aerofoil while dropping. Moreover, while dropping, the sodium hydroxide aqueous solution of 0.2N was dropped suitably to adjust pH from more than 10 to less than 11. From immediately after dropping the mixed aqueous solution of aluminum chloride and magnesium chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 µm. This precipitate was dried at 70° C. for 15 hours with the filter paper. The weight of the dried precipitate was 3.56 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro-octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 2 ppm. Therefore, the fixing ratio of the per-fluoro-octanoic acid contained in the layered double hydroxide was 98.6%. Moreover, the concentration of poly-tetra-fluoro-ethylene in the supernatant liquor was less than 50 ppm, and this precipitation rate was more than 98%.

EXAMPLE 4

Al—Zn System, Recovery with Sulfuric Acid

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 500 ppm. The sodium hydroxide aqueous solution of 0.2N was added to this wastewater to adjust pH to 7. The liquid temperature was 26° C. Next, about 100 mL of the mixed aqueous solution of aluminum chloride and zinc chloride was dropped in 20 L of said waste water for 3 hours, wherein $Al^{3+}$ ion was 30.2 mmol (1.3 times mol of APFO in the wastewater) and $Zn^{2+}$ ion was 69.6 mmol (3.0 times mol of APFO in the wastewater) in the mixed aqueous solution. In addition, this aqueous solution was stirred by 75 rpm using the anchor aerofoil while dropping. Moreover, while dropping, the sodium hydroxide aqueous solution of 0.2N was dropped suitably to adjust pH from more than 6.5 to less than 7.5. From immediately after dropping the mixed aqueous solution of aluminum chloride and zinc chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 µm. This precipitate was dried at 70° C. for 15 hours with the filter paper. The weight of the precipitate after drying was 65.2 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 3 ppm. Therefore, the fixing ratio of the per-fluoro-octanoic acid contained in the layered double hydroxide was 99.4%. Moreover, the concentration of poly-tetra-fluoro-ethylene of supernatant liquor was less than 50 ppm, and this precipitation rate was more than 98%.

In addition, 40 g of this dried precipitate was added to 120 g of dilute sulfuric acid, where the concentration was 10%, and this aqueous solution was stirred at room temperature for 3 hours. After this process, this solution was heated at 70° C. to filter the insoluble solid part. The weight of the filtered solid part was 27.6 g after drying. When this filtered solid part was analyzed by DTA and IR, the peaks belonging to the poly-tetra-fluoro-ethylene resin were detected. On the other hand, the filtrate was put quietly at 70° C. to separate the aqueous solution of the upper layer containing Zn ion and Al ion, and the oil layer of the lower layer. Then, the oil layer was taken out to be distilled, and 4.0 g of per-fluoro-octanoic acid was obtained.

EXAMPLE 5

Al—Mg System, Recovery with Sulfuric Acid

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 500 ppm. The sodium hydroxide aqueous solution of 0.2N was added to this wastewater to adjust pH to 7. The liquid temperature was 26° C. Next, about 1000 mL of the mixed aqueous solution of aluminum chloride and magnesium chloride was dropped in 20 L of the wastewater for 3 hours, wherein $Al^{3+}$ ion was 46.4 mmol (2.0 times mol of APFO in the wastewater) and $Mg^{2+}$ ion was 92.8 mmol (4.0 times mol of APFO in the wastewater) in the mixed aqueous solution. In addition, this aqueous solution was stirred by 50 rpm using the anchor aerofoil while dropping. Moreover, while dropping, the sodium hydroxide aqueous solution of 0.2N was dropped suitably to adjust pH from more than 9 to less than 10. From immediately after dropping the mixed aqueous solution of aluminum chloride and magnesium chloride, the very thin milk white liquid began to coagulate to form the white precipitate. The formation of the precipitate was finished after starting the dropping of this mixed aqueous solution in 3 hours. When the stirring was stopped, the formed precipitate fell down rapidly to be completed in about 5 minutes. The supernatant liquor was transparent and colorless. The precipitate was filtered by the membrane filter of 3 μm. This precipitate was dried until to the constant weight at 70° C. with the filter paper. The weight of the dried precipitate was 66.6 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 3 ppm. Therefore, the fixing ratio of the per-fluoro-octanoic acid contained in the layered double hydroxide was 99.4%. Moreover, the concentration of poly-tetra-fluoro-ethylene in the supernatant liquor was less than 50 ppm, and this precipitation rate was more than 98%.

In addition, 40 g of this dried precipitate was added to 120 g of dilute sulfuric acid, where the concentration was 10%, and this aqueous solution was stirred at room temperature for 3 hours Then, said solution was heated at 70° C. to filter the insoluble solid part. The weight of the filtered solid part after drying was 27.0 g. When this filtered solid part was analyzed by DTA and IR, the peaks belonging to the poly-tetra-fluoro-ethylene resin were detected. On the other hand, the filtrate was put quietly at 70° C. to separate the aqueous solution containing Al ion and Mg ion of the upper layer and the oil layer of the lower layer. Then, the oil layer was taken out to be distilled, and 4.0 g of per-fluoro-octanoic acid was obtained.

EXAMPLE 6

Al—Zn System, Recovery with Hydrochloric Acid

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 500 ppm. The sodium hydroxide aqueous solution of 0.2N was added to this wastewater to adjust pH to 7. The liquid temperature was 26° C. Next, about 100 mL of the mixed aqueous solution of aluminum chloride and zinc chloride was dropped in 20 L of said wastewater for 3 hours, wherein $Al^{3+}$ ion was 30.2 mmol (1.3 times mol of APFO in the wastewater) and $Zn^{2+}$ ion was 69.6 mmol (3.0 times mol of APFO in the wastewater) in the mixed aqueous solution. In addition, this aqueous solution was stirred by 75 rpm using the anchor aerofoil while dropping. Moreover, while dropping, the sodium hydroxide aqueous solution of 0.2N was dropped suitably to adjust pH from more than 6.5 to less than 7.5. From immediately after dropping of the mixed aqueous solution of aluminum chloride and zinc chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 μm. This precipitate was dried at 70° C. for 15 hours with the filter paper. The weight of the dried precipitate was 65.0 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When supernatant liquor was analyzed, the concentration of per-fluoro-octanoic acid ammonium was 3 ppm. Therefore, the fixing ratio of the per-fluoro-octanoic acid contained in the layered double hydroxide was 99.4%. Moreover, the concentration of poly-tetra-fluoro-ethylene of the supernatant liquor was less than 50 ppm, and this precipitation ratio was more than 98%.

In addition, 40 g of this dried precipitate was added to 120 g of concentrated hydrochloric acid, and this aqueous solution was stirred at room temperature for 3 hours. Then, said solution was heated at 70° C. to filter the insoluble solid part. The weight of the filtered solid part after drying was 27.8 g. When this filtered solid part was analyzed by DTA and IR, the peaks belonging to the poly-tetra-fluoro-ethylene resin were detected. On the other hand, the filtrate was put quietly at 70° C. to separate the aqueous solution containing Zn ion and Al ion of the upper layer, and the oil layer of the lower layer. Then, the oil layer was taken out to be distilled, and 3.9 g of per-fluoro-octanoic acid was obtained.

EXAMPLE 7

Al—Mg System, Putting Quietly the Insoluble Solid Part without Separation

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 500 ppm. The sodium hydroxide aqueous solution of 0.2N was added to this wastewater to adjust pH to 7. The liquid temperature was 26° C. Next, about 100 mL of the mixed aqueous solution of aluminum chloride and magnesium chloride was dropped in 20 L of said wastewater for 3 hours, wherein $Al^{3+}$ ion was 46.4 mmol (2.0 times mol of APF0 in the wastewater) and $Mg^{2+}$ ion was 92.8 mmol (4.0 times mol of APF0 in the wastewater) in the mixed aqueous solution. In addition, this aqueous solution was stirred by 50 rpm using the anchor aerofoil while dropping. Moreover, while dropping, the sodium hydroxide aqueous solution of 0.2N was dropped suitably to adjust pH from more than 9 to less than 10. From immediately after dropping the mixed aqueous solution of aluminum chloride and magnesium chloride, the very thin milk white liquid began to coagulate to form the white precipitate. The formation of the precipitate was finished after starting the dropping of this mixed aqueous solution in 3 hours. When the stirring was stopped, the formed precipitate fell down rapidly to be completed in about 5 minutes. The supernatant liquor was transparent and colorless. The precipitate was filtered by the membrane filter of 3 μm. This precipitate was dried until to the constant weight at 70° C. with the filter paper. The weight of the dried precipitate was 66.6 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro-octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 3 ppm. Therefore, the fixing ratio of the per-fluoro octanoic acid contained in the layered double hydroxide was 99.4%. Moreover, the concentration of poly-tetra-fluoro-ethylene of the supernatant liquor was less than 50 ppm, and this precipitation rate was more than 98%.

In addition, 40 g of this dried precipitate was added to 120 g of dilute sulfuric acid, where the concentration was 10%, and this aqueous solution was stirred at room temperature for 3 hours. Then, said solution was heated at 70° C. to be put quietly with this liquid temperature without filtering the insoluble solid part, so that the aqueous solution containing Al ion and Mg ion of the upper layer and the oil layer of the lower layer, were separated. Then, the oil layer was taken out to be distilled, and 4.1 g of per-fluoro-octanoic acid was obtained.

EXAMPLE 8

Al—Ca System

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 1000 ppm. In addition, after the pretreatment to remove the influence of the poly-tetra-fluoro-ethylene resin particles, which were remained in the wastewater, the absorbance was measured. The sodium hydroxide aqueous solution of 0.2N was added to this wastewater to adjust pH to 7. The liquid temperature was 26° C. Next, about 10 mL of the mixed aqueous solution of aluminum chloride and calcium chloride was dropped in 1 L of said wastewater for 3 hours, wherein $Al^{3+}$ion was 2.32 mmol (1.0 time mol of APF0 in the wastewater) and $Ca^{2+}$ ion was 4.64 mmol (2.0 times mol of APF0 in the wastewater) in the mixed aqueous solution. In addition, this aqueous solution was stirred by 50 rpm using the anchor aerofoil while dropping. Moreover, while dropping, the sodium hydroxide aqueous solution of 0.2N was dropped suitably to adjust pH from more than 9 to less than 10. From immediately after dropping the mixed aqueous solution of aluminum chloride and calcium chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 μm. This precipitate was dried at 70° C. for 15 hours with the filter paper. The weight of the dried precipitate was 3.22 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro-octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 344 ppm. Therefore, the fixing ratio of the per-fluoro-octanoic acid contained in the layered double hydroxide was 65.6%. Moreover, the concentration of poly-tetra-fluoro-ethylene of supernatant liquor was less than 50 ppm, and this precipitation rate was more than 98%.

EXAMPLE 9

Al—Mg System/$C_9F_{19}COONH_4$

Regarding the coagulated wastewater of the poly-tetra-fluoro-ethylene resin after the emulsion polymerization, where PTFE concentration was 2300 ppm, the concentration of per-fluoro-decanoic acid ammonium ($C_9F_{19}COONH_4$) was measured to be 500 ppm. The sodium hydroxide aqueous solution of 0.2N was added to this wastewater to adjust pH to 10. The liquid temperature was 26° C. Next, about 100 mL of the mixed aqueous solution of aluminum chloride and magnesium chloride was dropped in 1 L of said wastewater for 3 hours, wherein $Al^{3+}$ ion was 1.88 mmol (2.0 times mol of APF0 in the wastewater) and $Mg^{2+}$ ion was 3.77 mmol (4.0 times mol of APF0 in the wastewater) in the mixed aqueous solution. In addition, this aqueous solution was stirred by 50 rpm using the anchor aerofoil while dropping. Moreover, while dropping, the sodium hydroxide aqueous solution of 0.2N was dropped suitably to adjust pH from more than 9 to less than 10. From immediately after dropping of the mixed aqueous solution of aluminum chloride and magnesium chloride, the very thin milk white liquid began to coagulate to form the white precipitate. The formation of the precipitate was finished in 3 hours after starting the dropping this mixed aqueous solution. When the stirring was stopped, the formed precipitate fell down rapidly to be completed in about 5 minutes. The supernatant liquor was transparent and colorless. The precipitate was filtered by the membrane filter of 3 μm. This precipitate was dried until to the constant weight at 70° C. with the filter paper. The weight of the dried precipitate was 2.82 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro decanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-decanoic acid ammonium was 3 ppm. Therefore, the fixing ratio of the per-fluoro-decanoic acid contained in the layered double hydroxide was 99.4%. Moreover, the concentration of poly-tetra-fluoro-ethylene of supernatant liquor was less than 50 ppm, and this precipitation rate was more than 98%.

EXAMPLE 10

Al—Zn System/Formation Temperature of LHD was 60° C.

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 148 ppm. The sodium hydroxide aqueous solution of 0.2N was added to this wastewater to adjust pH to 7. In addition, this aqueous solution was heated to keep the temperature of 60° C. to 70° C. Next, about 10 mL of the mixed aqueous solution of aluminum chloride and zinc chloride was dropped in 1 L of said wastewater for 3 hours, wherein $Al^{3+}$ ion was 0.378 mmol (1.1 times mol of APF0 in the wastewater) and $Zn^{2+}$ ion was 0.755 mmol (2.2 times mol of APF0 in the wastewater) in the mixed aqueous solution. In addition, this aqueous solution was stirred by 50 rpm using the anchor aerofoil while dropping. Moreover, while dropping, the sodium hydroxide aqueous solution of 0.2N was dropped suitably to adjust pH from more than 6.5 to less than 7.5. From immediately after dropping the mixed aqueous solution of aluminum chloride and zinc chloride, the very thin milk white liquid began to coagulate to form the white precipitate. The formation of the precipitate was finished in 3 hours after starting the dropping of this mixed aqueous solution. When the stirring was stopped, the formed precipitate fell down rapidly to be completed in about 5 minutes. The supernatant liquor was transparent and colorless. The precipitate was filtered by the membrane filter of 3 μm. This precipitate was dried at 70° C. for 15 hours with the filter paper. The weight of the dried precipitate was 2.62 g. When the dried precipitate was analyzed by the differential thermogravimetric analysis (DTA), the infrared absorption spectrum (IR), and XRD, the peaks belonging to the poly-tetra-fluoro-ethylene resin, the negative ion surface-active agent (per-fluoro octanoic acid), and the layered double hydroxide, were detected. From these results, it was confirmed that the precipitate comprised the substance that the poly-tetra-fluoro-ethylene resin and the negative ion surface-active agent were precipitated with the layered double hydroxide. When the supernatant liquor was analyzed, the concentration of per-fluoro-octanoic acid ammonium was 13 ppm. Therefore, the fixing ratio of the per-fluoro-octanoic acid contained in the layered double hydroxide was 91.2%. Moreover, the concentration of poly-tetra-fluoro-ethylene of the supernatant liquor was less than 50 ppm, and this precipitation rate was more than 98%.

EXAMPLE 11

Regarding the coagulated wastewater of the poly-tetra-fluoro-ethylene resin after the emulsion polymerization, where PTFE concentration was 2300 ppm, the concentration of per-fluoro-octanoic acid ammonium ($C_7F_{15}COONH_4$) was measured to be 500 ppm. The sodium hydroxide aqueous solution of 0.2N was added to this wastewater to adjust pH to 7. The liquid temperature was 26° C. Next, about 10 mL of the mixed aqueous solution of aluminum chloride, zinc chloride, and magnesium chloride was dropped in said waste water for 3 hours, wherein $Al^{3+}$ ion was 0.232 mmol (1.0 time mol of APF0 in the wastewater), $Zn^{2+}$ ion was 0.232 mmol (1.0 time mol of APF0 in the wastewater), and $Mg^{2+}$ ion was 0.232 mmol (1.0 time mol of APF0 in the wastewater) in the mixed aqueous solution. Then, the precipitate was formed by the same processes as the Example 1 excepting to adjust PH of the solution from 8 to 9. The weight of the dried precipitate was 2.32 g. Moreover, regarding said precipitate, it was confirmed that the precipitate comprised the substance that the poly-tetra-fluoro-ethylene resin and the negative ion surface-active agent were precipitated with the layered double hydroxide, by the same processes as Example 1. When the supernatant liquor was analyzed, the concentration of per-fluoro-octanoic acid ammonium was 4 ppm. Therefore, the fixing ratio of the per-fluoro-octanoic acid contained in the layered double hydroxide was 96%. Moreover, the concentration of poly-tetra-fluoro-ethylene of the supernatant liquor was less than 50 ppm, and this precipitation rate was more than 98%.

[Industrial Applicability]

According to the process of the present invention, the followings are possible. The fluorine compound, such as the surface-active agent having the per-fluorocarbon chain, can be absorbed and fixed stably between the layers of the layered double hydroxide, and the polymer containing fluorine in the solution, such as PTFE, can be coagulated and precipitated simultaneously. The formation of the layered double hydroxide and the absorption of the fluorine compound are advanced simultaneously in the solution, and this layered double hydroxide is formed easily by adding the divalent and trivalent metal salts, so that the above-mentioned fluorine compound can be absorbed and fixed easily. Moreover, in the suitable embodiment, when the concentration of the anion aqueous solution of the surface-active agent having the per-fluorocarbon chain is less than several % by weight, for example, very low concentration of about 0.01% by weight, this fluorine compound can be fixed at a very high rate of more than 90%. In addition, as the additional metal salts, the safe salts to environment can be used. Moreover, since the layered double hydroxide can be recovered as a solid, it is advantageously in transportation or storage. Furthermore, according to the treatment process of the present invention, the fluorine compound fixed in the layered double hydroxide can be recovered efficiently for reuse by the separation. Therefore, the burden to environment and ecosystem with the fluorine compound can be reduced, and the fluorine compound can be reused as the resources. In addition, since the polymer containing fluorine in the solution, such as PTFE, can be coagulated and precipitated by fixing of the fluorine compound, the coagulated wastewater of the polymer containing fluorine can be treated effectively, in which such wastewater is drawn off in the production process, such as the emulsion polymerization process of PTFE (poly-tetra-fluoro-ethylene) and the manufacturing process of the electronic parts industry.

recovering a solid part by a solid-liquid separation, dissolving said recovered solid part in an acid, and separating the fluorine compound or its salt.

3. The treatment process of the solution containing the fluorine compound and the polymer containing fluorine according to claim 1, the process further comprising,
adjusting pH of the solution to more than 4,

TABLE 1

| No. | Fluorine Compound in solution Kinds | Concentration | Polymer Containing Fluorine in solution | Additional Metal Salts mmol Trivalent | Divalent | pH Adjustment | Precipitate Weight (g) | Fixing Ratio of Anion % | Precipitation Rate of Polymer % | Concentration in Supernation liquor Anion | Polymer |
|---|---|---|---|---|---|---|---|---|---|---|---|
| 1 | Per·fluoro·octanoic acid ammonium ($C_7F_{15}COONH_4$) | 148 ppm 1 L | PTFE 2300 ppm | Al 0.378 (1.1) | Zn 0.755 (2.2) | 6.5~7.5 | 2.50 | 98.6 | 98% | 2 ppm | <50 ppm |
| 2 | Per·fluoro·octanoic acid ammonium ($C_7F_{15}COONH_4$) | 200 ppm 1 L | PTFE 2300 ppm | Al 0.603 (1.3) | Mg 1.21 (2.6) | 9~10 | 2.54 | 95.9 | 98% | 8 ppm | <50 ppm |
| 3 | Per·fluoro·octanoic acid ammonium ($C_7F_{15}COONH_4$) | 148 ppm 1 L | PTFE 2300 ppm | Al 4.46 (1.3) | Mg 8.92 (2.6) | 10~11 | 3.56 | 98.6 | 98% | 2 ppm | <50 ppm |
| 4 | Per·fluoro·octanoic acid ammonium ($C_7F_{15}COONH_4$) | 500 ppm 20 L | PTFE 2300 ppm | Al 30.2 (1.3) | Zn 69.6 (3.0) | 6.5~7.5 | 65.2 | 99.4 | 98% | 3 ppm | <50 ppm |
| 5 | Per·fluoro·octanoic acid ammonium ($C_7F_{15}COONH_4$) | 500 ppm 20 L | PTFE 2300 ppm | Al 46.4 (2.0) | Mg 92.8 (4.0) | 9~10 | 66.6 | 99.4 | 98% | 3 ppm | <50 ppm |
| 6 | Same conditions of precipitate formation as No. 4, Recovered precipitate is dissolved in concentrated hydrochloric acid to recover per·flouro·octanoic acid | | | | | | | | | | |
| 7 | Same conditions of precipitate formation as No. 5, Recovered precipitate is dissolved in dilute sulfuric acid to take out an oil layer of per·flouo·ocatnoic acid without filtering undissolved | | | | | | | | | | |
| 8 | Per·fluoro·octanoic acid ammonium ($C_7F_{15}COONH_4$) | 1000 ppm 1 L | PTFE 2300 ppm | Al 2.32 (1.0) | Ca 4.64 (2.0) | 9~10 | 3.22 | 65.6 | 98% | 344 ppm | <50 ppm |
| 9 | Per·fluoro·decanoic acid ammonium ($C_9F_{19}COONH_4$) | 500 ppm 1 L | PTFE 2300 ppm | Al 1.88 (2.0) | Mg 3.77 (4.0) | 9~10 | 2.82 | 99.4 | 98% | 3 ppm | <50 ppm |
| 10 | Per·fluoro·octanoic acid ammonium (Liquid Temperature 50–60° C.) | 148 ppm 1 L | PTFE 2300 ppm | Al 0.378 (1.1) | Zn 0.755 (2.2) | 6.5~7.5 | 2.62 | 91.2 | 98% | 13 ppm | <50 ppm |
| 11 | Per·fluoro·octanoic acid ammonium ($C_7F_{15}COONH_4$) | 100 ppm 1 L | PTFE 2300 ppm | Al 0.232 | Zn: 0.232 Mg: 0.232 | 8~9 | 2.32 | 96.0 | 98% | 4 ppm | <50 ppm |

(Note) The value of ( ) of metal salt concentration is mole ratio. The precipitate weight is a dried weight (g). The fixing ratio of anions is (%) to the initial concentration of a fluorine compound. The precipitation rate of polymer is a precipitated weight (%) to the intitial concentration of a polymer containing fluorine. An anion in the supernatant liquor is a fluorine compound. The liquid temperature excepting No. 10 is 26° C.

What is claimed is:

1. A treatment process of a solution containing an organic compound having a fluorocarbon chain (hereinafter the fluorine compound) and a polymer containing fluorine, the process comprising,
adding divalent and trivalent metal salts to said solution,
forming a layered double hydroxide having the fluorine compound between layers to fix the fluorine compound, and
precipitating said layered double hydroxide with the polymer containing fluorine.

2. A treatment process of a solution containing an organic compound having a fluorocarbon chain, hereinafter the fluorine compound, and a polymer containing fluorine, the process comprising,
adding divalent and trivalent metal salts to said solution,
forming a layered double hydroxide having the fluorine compound between layers to fix the fluorine compound,
precipitating said layered double hydroxide having the fluorine compound between layers and the polymer containing fluorine, precipitating the layered double hydroxide having the fluorine compound between layers and the polymer containing fluorine compound.

4. The treatment process of the solution containing the fluorine compound and the polymer containing fluorine according to claim 1, the process further comprising,
adding an alkali to the solution to adjust pH from 4 to 12,
adding divalent and trivalent metal salts to said solution, and
precipitating the layered double hydroxide having the fluorine compound between layers and the polymer containing fluorine.

5. The treatment process of the solution containing the fluorine compound and the polymer containing fluorine according to claim 1,
wherein the divalent metal salt is a salt of magnesium, calcium, zinc, nickel, copper, manganese (divalent), or cobalt (divalent), and the trivalent metal salt is a salt of aluminum, iron, chromium, manganese (trivalent), cobalt (trivalent), potassium, lanthanum, or scandium.

6. The treatment process of the solution containing the fluorine compound and the polymer containing fluorine according to claim 1, wherein the divalent and the trivalent metal salts are chlorides.

7. The treatment process of the solution containing the fluorine compound and the polymer containing fluorine according to claim 1,
wherein said fluorine compound is a carboxylic acid or a sulfonic acid having a fluorocarbon chain, in which the number of carbon is more than 5.

8. The treatment process of the solution containing the fluorine compound and the polymer containing fluorine according to claim 1,
wherein the polymer containing fluorine is poly-tetra-fluoro-ethylene.

9. The treatment process of the solution containing the fluorine compound and the polymer containing fluorine according to claim 1,
wherein the layered double hydroxide having the fluorine compound between layers is shown in the following formula [1]:

$$M(II)_{1-x}M(III)_x(OH)_2Y_{x/m} \cdot nH_2O \quad [1]$$

where Y is an anion having valence number m of the fluorine compound having the fluorocarbon chain, M(II) is a divalent metal ion, M(III) is a trivalent metal ion, X is 0.1 to 0.5, and n is 0 or positive integer.

10. A treatment process for recovering an organic compound having a fluorocarbon chain, hereinafter the fluorine compound, and its salts, the process comprising,
precipitating the layered double hydroxide and the polymer containing fluorine by the treatment process according to claim 1,
recovering the solid part by solid-liquid separation,
dissolving said recovered solid part in a mineral acid to recover the separated fluorine compound or its salts, or heating said mineral acid dissolving the recovered solid part,
putting quietly to separate an oil layer, and
taking out an oil layer to recover the fluorine compound and its salts.

11. A treatment process for recovering an organic compound having a fluorocarbon chain, hereinafter the fluorine compound, and its salts, the process comprising,
precipitating the layered double hydroxide and the polymer containing fluorine by the treatment process according to claim 1,
recovering the solid art by solid-liquid separation,
contacting said separated solid part with a sodium carbonate aqueous solution,
recovering the solid part by solid-liquid separation,
dispersing the recovered solid part to an organic solvent, and
filtering an insoluble solid part from said solvent.

12. The treatment process of the solution containing the fluorine compound and the polymer containing fluorine according to claim 2, the process further comprising,
adjusting pH of the solution to more than 4,
precipitating the layered double hydroxide having the fluorine compound between layers and the polymer containing fluorine compound.

13. The treatment process of the solution containing the fluorine compound and the polymer containing fluorine according to claim 2, the process further comprising,
adding an alkali to the solution to adjust pH from 4 to 12,
adding divalent and trivalent metal salts to said solution, and
precipitating the layered double hydroxide having the fluorine compound between layers and the polymer containing fluorine.

14. The treatment process of the solution containing the fluorine compound and the polymer containing fluorine according to claim 2,
wherein the divalent metal salt is a salt of magnesium, calcium, zinc, nickel, copper, manganese (divalent), or cobalt (divalent), and the trivalent metal salt is a salt of aluminum, iron, chromium, manganese (trivalent), cobalt (trivalent), potassium, lanthanum, or scandium.

15. The treatment process of the solution containing the fluorine compound and the polymer containing fluorine according to claim 2, wherein the divalent and the trivalent metal salts are chlorides.

16. The treatment process of the solution containing the fluorine compound and the polymer containing fluorine according to claim 2,
wherein said fluorine compound is a carboxylic acid or a sulfonic acid having a fluorocarbon chain, in which the number of carbon is more than 5.

17. The treatment process of the solution containing the fluorine compound and the polymer containing fluorine according to claim 2,
wherein the polymer containing fluorine is poly-tetra-fluoro-ethylene.

18. The treatment process of the solution containing the fluorine compound and the polymer containing fluorine according to claim 2,
wherein the layered double hydroxide having the fluorine compound between layers is shown in the following formula [1], $$M(II)_{1-x}M(III)_x(OH)_2Y_{x/m} \cdot nH_2O \quad [1]$$

where Y is an anion having valence number m of the fluorine compound having the fluorocarbon chain, M(II) is a divalent metal ion, M(III) is a trivalent metal ion, X is 0.1 to 0.5, and n is 0 or positive integer.

19. A treatment process for recovering an organic compound having a fluorocarbon chain, hereinafter the fluorine compound, and its salts, the process comprising,
precipitating the layered double hydroxide and the polymer containing fluorine by the treatment process according to claim 2,
recovering the solid part by solid-liquid separation,
dissolving said recovered solid part in a mineral acid to recover the separated fluorine compound or its salts, or heating said mineral acid dissolving the recovered solid part,
putting quietly to separate an oil layer, and
taking out an oil layer to recover the fluorine compound and its salts.

20. A treatment process for recovering an organic compound having a fluorocarbon chain, hereinafter the fluorine compound, and its salts, the process comprising,
precipitating the layered double hydroxide and the polymer containing fluorine by the treatment process according to claim 2,
recovering the solid art by solid-liquid separation,
contacting said separated solid part with a sodium carbonate aqueous solution,
recovering the solid part by the solid-liquid separation,
dispersing the recovered solid part to an organic solvent, and
filtering an insoluble solid part from said solvent.

* * * * *